United States Patent [19]
Umezawa et al.

[11] Patent Number: 5,096,888
[45] Date of Patent: Mar. 17, 1992

[54] 3-DEOXY MYCAMINOSYL TYLONOLIDE DERIVATIVES

[75] Inventors: Sumio Umezawa, Tokyo; Tsutomu Tsuchiya, Kanagawa; Tomio Takeuchi, Tokyo; Shunji Kageyama, Ibaraki; Shuichi Sakamoto, Tokyo, all of Japan

[73] Assignee: Zaidan Hojin Biseibutsu Kagaku Kenkyikai, Tokyo, Japan

[21] Appl. No.: 586,905

[22] Filed: Sep. 24, 1990

Related U.S. Application Data

[63] Continuation of Ser. No. 362,872, Jun. 7, 1989, abandoned.

[30] Foreign Application Priority Data

Jun. 13, 1988 [JP] Japan ................................. 63-146410
Jan. 18, 1989 [JP] Japan ..................................... 1-9160

[51] Int. Cl.$^5$ ..................... A61K 31/70; C07H 17/08
[52] U.S. Cl. .................................... 514/30; 536/7.1
[58] Field of Search ............................. 536/7.1; 514/30

[56] References Cited

U.S. PATENT DOCUMENTS

| | | | |
|---|---|---|---|
| 4,345,069 | 8/1982 | Sakakibara et al. | 536/7.1 |
| 4,438,109 | 3/1984 | Umezawa et al. | 536/7.1 |
| 4,794,173 | 12/1988 | Umezawa et al. | 536/7.1 |

FOREIGN PATENT DOCUMENTS 2221695 9/1987 Japan ..................... 536/7.1

*Primary Examiner*—Johnnie R. Brown
*Assistant Examiner*—Elli Peselev
*Attorney, Agent, or Firm*—Burgess, Ryan & Wayne

[57] ABSTRACT

3-Deoxy mycaminosyl tylonolide derivatives represented by the following general formula and salts thereof:

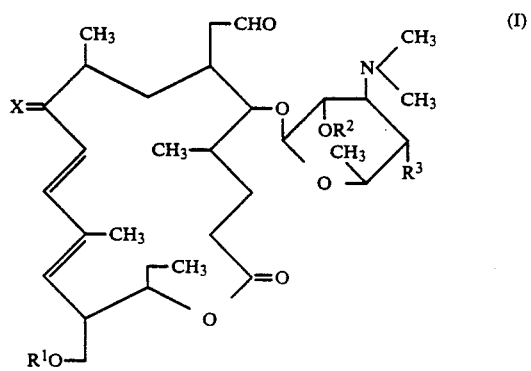

wherein X represents an oxygen atom or $=N-OR^4$ (wherein $R^4$ represents hydrogen or lower alkyl); $R^1$ represents a hydrogen atom, an acyl group or an alkylsilyl group; $R^2$ represents a hydrogen atom or an acyl group; and $R^3$ represents a hydrogen atom or a hydroxyl group. The compounds of this invention of the formula (I) are novel compounds and have excellent antibacterial activity.

5 Claims, No Drawings

3-DEOXY MYCAMINOSYL TYLONOLIDE DERIVATIVES

This is a division of application Ser. No. 362,872, filed June 7, 1989, now abandoned.

DETAILED DESCRIPTION OF INVENTION

1. Field of the Invention

The present invention relates to macrolactone compounds having excellent antibacterial activity, and so the compounds are useful for medicaments (especially antibiotics) for the prevention or treatment of diseases caused by various bacteria. That is, the compounds of the present invention are 3-deoxy mycaminosyl tylonolide derivatives represented by the following formula, or salts thereof:

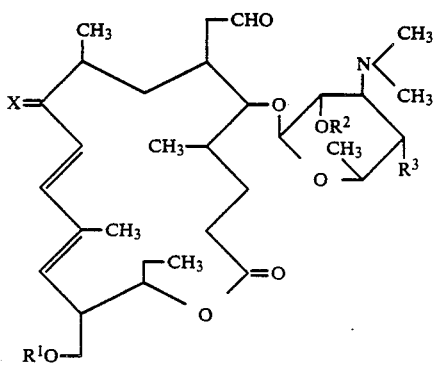

wherein X represents an oxygen atom or the formula: $=N-OR^4$ (wherein $R^4$ represents a hydrogen atom or a lower alkyl group); $R^1$ represents a hydrogen atom, an acyl group or an alkylsilyl group; $R^2$ represents a hydrogen atom or an acyl group; and $R^3$ represents a hydrogen atom or a hydroxyl group.

2. Prior Art and Problems to be Solved by the Present Invention

The compounds of the present invention are novel compounds and have chemical-structural characteristics in that the compounds may have acyl group(s) at the 2'- and/or 23-position(s) of 3,4'-di-deoxy mycaminosyl tylonolide compounds or of mycaminosyl tylonolide compounds. Such compounds have not been known until now.

In the foregoing definitions in the formula (I) compounds, the term "lower alkyl" means a straight or branched chain alkyl having 1 to 5 carbon atoms. Thus, examples of the "lower alkyl" are methyl, ethyl, propyl, iso-propyl, butyl, iso-butyl, tert-butyl, pentyl, 1-methylbutyl, 2-methylbutyl, neo-pentyl, etc.

The "alkyl" means a straight or branched chain alkyl having 1 to 10 carbon atoms. Thus, examples of the "alkyl" are, in addition to the examples of the foregoing the "lower alkyl", hexyl, 1-methylpentyl, 2-methylpentyl, thexyl, heptyl, 1-methylhexyl, 2-methylhexyl, 2-ethylpentyl, 1,3-dimethylpentyl, octyl, nonyl, decyl, etc. Thus, examples of the "alkylsilyl" are trimethylsilyl, triethylsilyl, tri(iso-propyl)silyl, tert-butyldimethylsilyl, tert-butyldiethylsilyl, thexyldimethylsilyl, etc.

Examples of the "acyl" are formyl, acetyl, propionyl, butyryl, iso-butyryl, valeryl, iso-valeryl, pipaloyl, hexanoyl, etc. (namely, alkanoyl groups); acryloyl, metacroyl, crotonoyl, etc. (namely, lower alkenoyl groups); benzoyl, toluoyl, xyloyl, etc, (namely, aroyl groups); phenylacetyl, phenylpropionyl, phenylhexanoyl, etc. (namely, phenyl(lower)alkanoyl groups).

By the way of the group "$N-OR^4$" have geometrical isomerism, and so, the compound (I) of the present invention may a mixture of such isomers, or each isomer (namely, syn- or anti-isomer).

The compounds of formula (I) may form salts and the present invention also includes the salts of the compounds of formula (I). Such salts include pharmaceutically acceptable salts, and are, for example, acid addition salts with mineral acids such as hydrochloric acid, sulfuric acid and the like, and with organic acids such as formic acid, toluenesulfonic acid.

Representative Preparation Methods

The formula (I) compound may be prepared by various methods. Hereinafter, the representative methods are illustrated.

Process variant 1

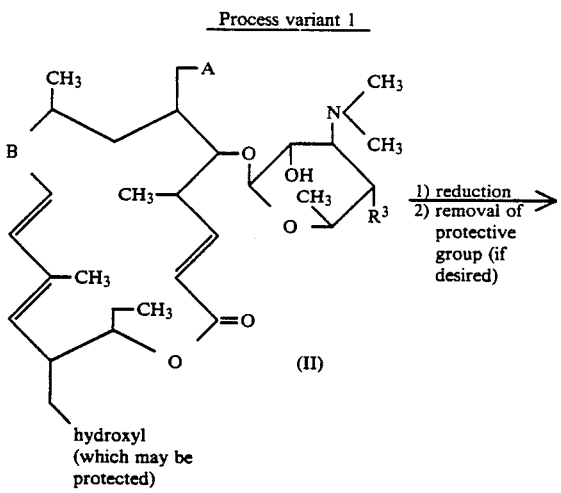

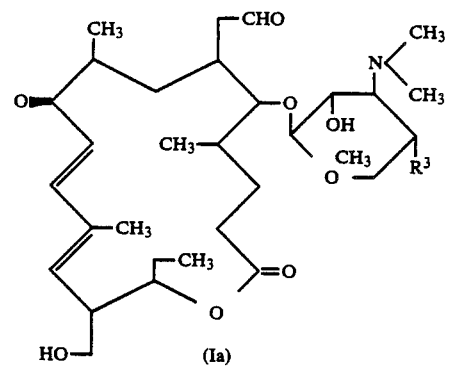

Process variant 2

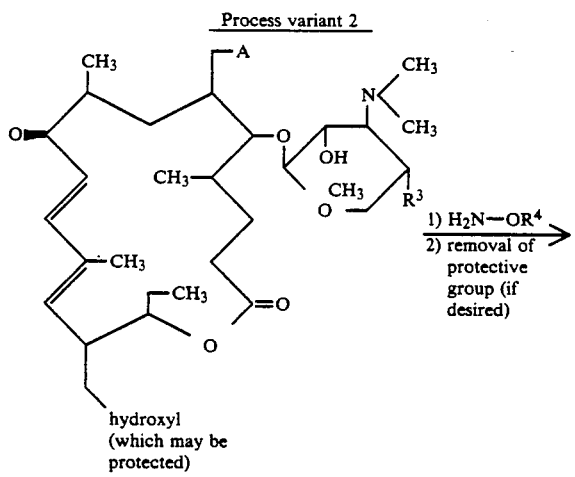

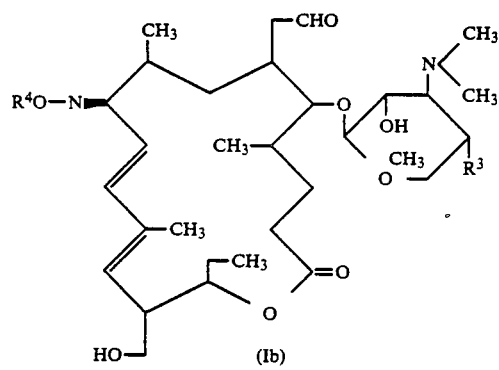

Process variant 3

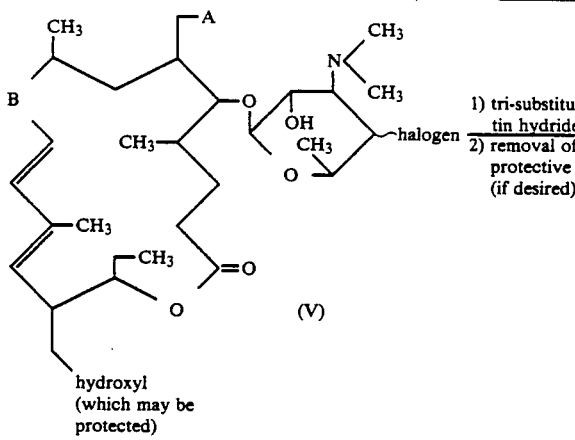

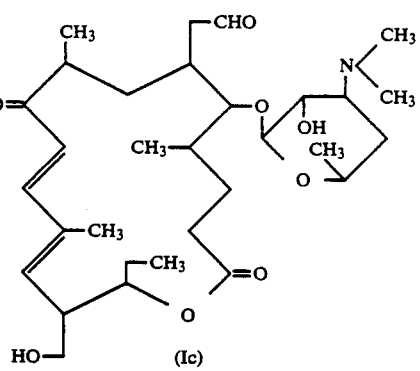

(In the above formula, A represents aldehyde group which may be protected, B represents carbonyl group which may be protected.)

Process Variant 1:

The formula ($I_a$) compounds in the present invention (namely, 3-deoxy compounds having 9-carbonyl group) can be prepared by applying reduction reaction to the formula (II) compounds (namely, the compounds having double bond at the 2-position) and, if desired, removing the protective group.

In the formula (II) compounds, as protected-aldehyde or protected-carbonyl, there are listed acetal (or thioacetal), ketal (thioketal) types, and examples of these are dimethylacetal (dimethylketal), diethylacetal (diethylketal), diethylthioacetal (diethylthioketal), ethyleneacetal (ethylenethioketal), propyleneacetal (propylene ketal) or those substituted by some group such as methyl.

Examples of protective group of hydroxyl are trimethylsilyl, triethylsilyl, tri(iso-propyl)silyl, tri(tert-butyl)silyl, tert-butyldimethylsilyl, tert-butyldiethylsilyl, thexyldimethylsilyl and the like (namely, silyl type protective group); acetyl, propionyl, butyryl, iso-butyryl, valeryl, iso-valeryl and the like (namely, alkanoyl type protective group); 2-tetrahydrofuran; 2-tetrahydropyranyl; and the like.

The reaction may be carried out in an inert solvent, such as benzene, toluene, ether, tetrahydrofuran, dimethylformamide, dimethylsulfoxyde and the like. The reduction reaction to the formula (II) compound may be, for example, carried out by treating with a reducing agent such as di-iso-butyl aluminum hydride.

The reaction temperature may be suitably controlled according to the kind of starting compound and reducing agent, etc., but, preferably, may be set at under cooling.

In the case of the formed compound having protective group, the protective group is removed, if desired. The removal of the protective group is performed in conventional manner, for example, by treating with mineral acid such as hydrochloric acid, sulfuric acid and the like or with organic acid such as trifluoroacetic acid and the like; in the case of the protective group being silyl type, the removal of the protective group is performed by treating by tetrabutylammoniumfluoride, hydrochloric acid, acetic acid, etc.

Process Variant 2

This method can be performed by reacting amino-compound ($H_2N$—$OR^4$) with the formula (III) compound (namely, mycaminosyl tylonolide wherein aldehyde group may be protected, or its 4'-deoxy derivative), and then by removing protective group in the case of aldehyde- or carbonyl-group being protected.

The reaction of the compound (III) and the compound (IV) can be carried out in an inert solvent; the formula (IV) compound may be in the form of free base or of salt with acid. In the case of the formula (IV) compound being in the form of free base, the reaction may be carried out after addition of acids such as pyridine-p-toluene-sulfonate, 10-camphorsulfonic acid and the like; in the case of the formula (IV) compound being in the form of acid addition salt, the reaction may be carried out after addition of inorganic base such as sodium hydrogen carbonate, sodium carbonate, potassium carbonate and the like, or addition of organic base such as pyridine, triethylamine, piperidine and the like. In the case of such acid or base being added, the pH of the reaction solution is, preferably, controlled to be set at 4-5. The reaction solvents are, for example, water, alcohol, tetrahydrofuran, acetonitrile, benzene and the like; The reaction is, preferably, performed under room temperature or heating (by refluxing) for 1-2 hours to 2-3 days.

The removal of the protective group of the formed compound can be carried out in conventional manner as described in the foregoing Process Variant 1.

Process Variant 3

The method is performed by replacing 4'-halogen atom with hydrogen atom, and the reaction can be carried out by subjecting a reducing agent (in particular, trisubstituted tin hydride) to the formula (V) compound.

Examples of trisubstituted tin hydride are triethyl tin hydride, tri-n-butyl tin hydride and the like (namely, trialkyltin hydride); triphenyl tin hydride (namely, triarkyl tin-hydride); and the like. Preferably examples of the reaction solvent are toluene, benzene, dioxane, tetrahydrofuran and the like (namely, aprotic solvent and having no halogen atom and being difficult to be reduced). The reaction may be performed under room temperature or under heating. If necessary, in order to initiate the reaction, radical initiator such as alpha, alpha-azobis-iso-butylonitrile may added to the reaction solution.

The protective group can be removed by in a conventional manner as described in the foregoing Process variant 1.

Process variant 4

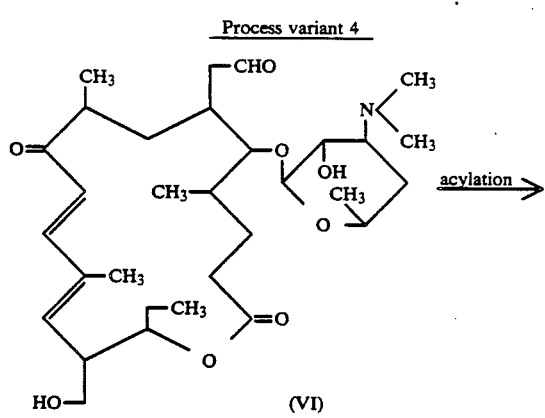

(VI)

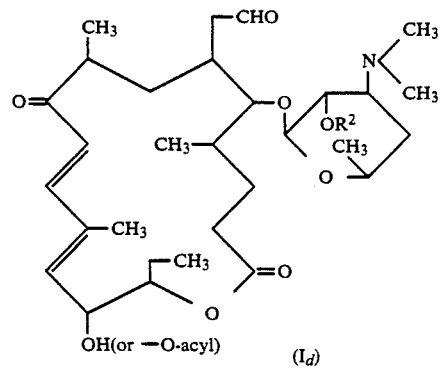

(I$_d$)

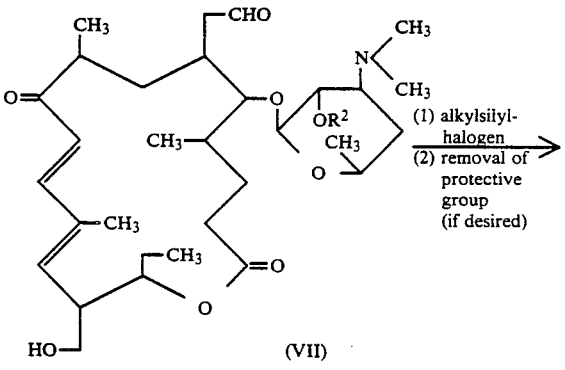

(VII)

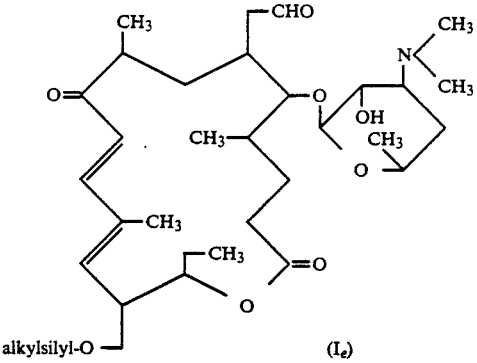

(I$_e$)

Explanation of Process Variant 4

The formula (I$_d$) compound of the present invention can be prepared by acylating the formula (VI) compounds (namely, 3,4'-dideoxy mycaminosyl tylonolide derivatives).

The acylating reaction may be performed by using various acylating agents such as acid halogenide (for example, acetyl chloride, acetyl bromide, propionyl chloride, pivaloyl chloride, benzoyl chloride), acid anhydride (e.g. acetic acid anhydride, benzoic acid anhydride), active ester (acid p-nitrophenyl ester, acid 2,4-dintrophenyl ester, etc.) under suitable reaction condition. The acid may be used in the form of free acid or its salt, and in this case, dehydrating agent such as hydrochloric acid or sulfuric acid, etc. is used for the reaction.

Examples of the reaction solvent are water, acetone, dioxane, acetonitrile, chloroform, benzene, dichloromethane, tetrahydrofuran, ethyl acetate, N,N-dimethylformamide, pyridine, (that is, any solvent which does not take part in the reaction); The solvents may be used as a mixture thereof. The reaction temperature may be suitably controlled, and preferably under cooling or under heating.

The stirring compound (VI) can be prepared in a method described in unexamined Japanese patent publication Sho. 63-146410.

Explanation of Process Variant 5

The formula ($I_e$) compound can be prepared by reacting the formula (VII) compound with alkylsilyl halide (alkylsilyl halogen), and then, if desired, removing 2'-acyl group.

Examples of alkylsily halide are trimethylsilyl chloride, triethylsilyl bromide, tert-butyldimethylsilyl chloride, thexyldimethylsilyl chloride. The reaction may be preferably performed in the presence of inorganic or organic base such as sodium carbonate, potassium carbonate, sodium hydrogen carbonate, pyridine, lutidine, picoline, imidazole. Examples of the reaction solvent are acetone, acetonitrile, tetrahydrofuran, benzene, chloroform, dimethylformamide.

The removal of acyl group of the formed compound can be performed by using inorganic acid such as hydrochloric acid, sulfuric acid, etc. or using organic acid such as trifluoroacetic acid, etc., or can be performed by allowing the formed compound to stand as it is, in alcohols such as methanol, ethanol, etc.

The formula (I) compound thus prepared may be separated and purified according to the conventional methods such as extraction, recrystallization, column chromatography, etc.

EFFECTS OF THE INVENTION

The compounds of this invention of formula (I) have shown antibacterial activity against various pathogens including gram-positive and -negative bacteria. Thus, the compounds are useful for medicaments (especially, antibiotics) for the prevention or treatment of diseases caused by such bacteria.

Concerning the antimicrobial activity of the compounds of this invention, the following experiment has been done.

Staph. aureus Smith (bacterial amount: $10^6$ CFU/mouse) were injected intraperitoneally into 6 healthy mice (one group), and after 2 hours each Sample was given orally, and survival number of after one week observed. The compounds of the present invention have shown the excellent in vivo preventing and treating effect ($ED_{50}$: 50-150 mg/kg).

Medicaments containing as a major component the compounds of the present invention or salts thereof may be prepared by using pharmaceutical carriers and excipients used in the relevant art according to the conventional method. The types of administration may include oral administration by tablets, granules, dusts, capsules and the like, or parenteral administration by injection and the like. The dosage may be suitably determined depending upon the conditions, but, for an adult, the total dosage is 50-2,000 mg per day, and this dosage is usually administered one to four times per day.

EXAMPLES

The following, Examples further detail the preparative methods of the compounds of this invention. Some of the starting compounds used for the synthesis thereof may be novel compounds, so their manufacturing methods are also shown in the following Reference Examples. In the following Examples, "Mass" means mass spectrum, and $^1$H-NMR means hydrogen nuclear magnetic resonance spectrum.

REFERENCE EXAMPLE 1

23-O-thexyldimethylsilyl-mycaminosyl tylonolide, 9,20-bis(ethyleneacetal)

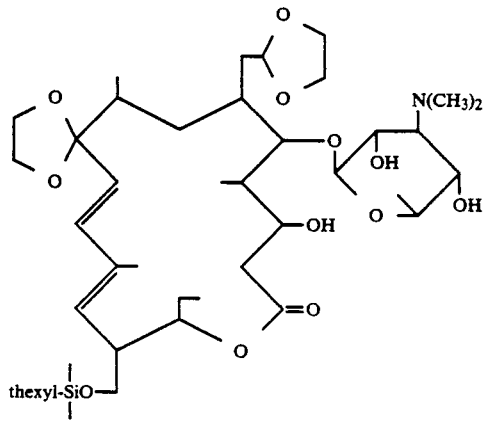

1,000 g of mycaminosyl tylonolide 9,20-bis(ethyleneacetal) was dissolved in 8 ml of dry dimethylformamide, and after adding thereto 200 mg of imidazole and 0.39 g of thexyl-dimethyl-silane chloride $$\begin{array}{c} (CH_3 \; CH_3 \qquad ), \\ | \quad | \\ CH-C-SiMe_2Cl \\ | \quad | \\ CH_3 \; CH_3 \end{array}$$

the reaction mixture was kept at room temperature for 6 hours. The reaction mixture was concentrated, and to the residue was added saturated aqueous sodium hydrogencarbonate (100 ml). The mixture thus formed was extracted with chloroform. The organic layer separated was washed with water, and dried to give a syrup, which was purified by chromatography (Wako gel C-200: 80 g; chloroform:methanol:conc. aqueous ammonia=15:1:0.1) to give 23-O-thexyldimethylsilyl mycaminosyl tylonolide 9,20-bis(ethyleneacetal) as solid material (1.12 g; yield 93%).

Physico-chemical character:

(i) $[\alpha]_D^{23}$: $-9°$ (c1, CHCl$_3$)

| (ii) Elemental analysis ($C_{43}H_{77}NO_{12}Si$) | | |
|---|---|---|
| C | H | N |
| Found (%) 61.95 | 9.20 | 1.68 |
| Calcd. (%) 62.36 | 9.37 | 1.69 |

(iii) Mass m/z=828 (M+)

REFERENCE EXAMPLE 2

2,40,4'-di-O-acetyl-23-O-thexyldimethylsilyl mycaminosyl tylonolide-9,20-bis(ethyleneacetal)

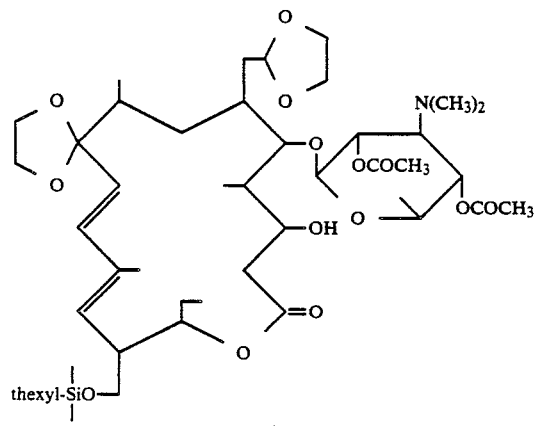

2.20 g of 23-O-thexyldimethylsilyl mycaminosyl tylonolide 9,20-bis(ethyleneacetal) was dissolved in 22 ml of dry acetonitrile, and after adding thereto 0.58 ml of acetic anhydride, the mixture was kept at room temperature overnight. The reaction mixture was concentrated, and after adding thereto saturated aqueous sodium hydrogencarbonate (100 ml), the mixture was extracted with toluene, and stirred. The organic layer was washed with water, dried, and concentrated to give solid material, which was purified by chromatography [silica gel] (Wako gel C-200: 200 g; cyclohexane:acetone= 7:2) to give colorless solid material of 2',4'-di-O-acetyl-23-O-thexyldimethylsilyl mycaminosyl tylonolide, 9,20-bis(ethyleneacetal) [2.04 g] (yield: 84%).

Physico-chemical character:

(i) $[\alpha]_D^{25}$: $-40°$ (c1, CHCl$_3$)

| (ii) Elemental analysis ($C_{47}H_{81}NO_{14}Si$) | | | |
|---|---|---|---|
| | C | H | N |
| Found. (%) | 61.79 | 8.96 | 1.48 |
| Cacld. (%) | 61.88 | 8.95 | 1.54 |

(iii) Mass m/z=912(M+)

(iv) $^1$H-NMR (CDCl$_3$ TMS internal standard) δ 2.00, 2.04 (each 3H, s, CH$_3$ of 2',4'—COCH$_3$).

REFERENCE EXAMPLE 3

2',4+-di-O-acetyl-3-O-mesyl-23-O-thexyldimethylsilyl mycaminosyl tylonolide-9,20-bis(ethyleneacetal)

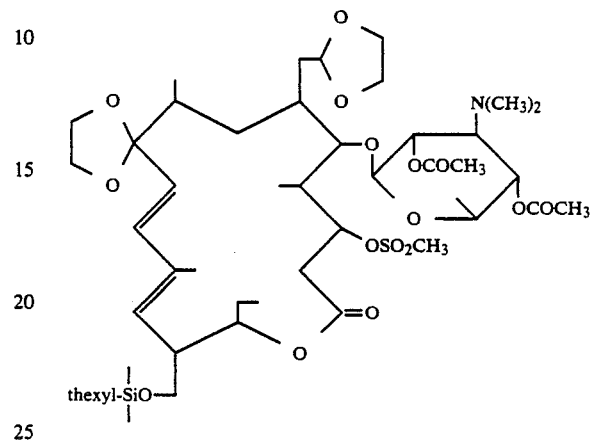

700 mg (0.77 mmol) of 2',4'-di-O-acetyl-23-O-thexyldimethylsilyl mycaminosyl tylonolide-9,20-bis(ethyleneacetal) was dissolved in 2 ml of dry pyridine, and after adding thereto 0.18 ml (2.3 mmol) of methanesulfonyl chloride, the mixture was kept at room temperature for 3 hours. The reaction solution was poured into 100 ml of saturated aqueous sodium hydrogen carbonate, and extracted with 50 ml of toluene 3 times. The organic layer thus obtained was washed with water, dired, and concentrated to give pale yellow syrup, which was purified by silica gel column chromatography (Wako gel C-200: 35 g; cyclohexane:acetone=3:1) to give 723 mg (yield: 95%) of colorless solid material of 2',4'-di-O-acetyl-3-O-mesyl-23-O-thexyldimethylsilyl mycaminosyl tylonolide, 9,20-bis(ethyleneacetal).

Physico-chemical character:

(i) $[\alpha]_D^{25}$: $-51°$ (c1, CHCl$_3$)

| (ii) Elemental analysis ($C_{48}H_{83}NO_{16}SSi$) | | | |
|---|---|---|---|
| | C | H | N |
| Found (%) | 58.04 | 8.62 | 1.36 |
| Cacld. (%) | 58.22 | 8.45 | 1.41 |

(iii) Mass m/z=990(M+)

(iv) $^1$H-NMR (CDCl$_3$, TMS) δ; 2.02, 2.04 (each 3H, s, CH$_3$ of 2',4'—COCH$_3$) 3.15 (3H, s, CH$_3$ of 3OSO$_2$CH$_3$)

REFERENCE EXAMPLE 4

2-dehydro-2-en-3-deoxy-23-O-thexyldimethylsilyl mycaminosyl tylonolide 9,20-bis(ethyleneacetal)

| (ii) Elemental analysis ($C_{43}H_{75}NO_{11}Si$) | | | |
|---|---|---|---|
| | C | H | N |
| Found (%) | 63.47 | 9.36 | 1.68 |
| Cacld. (%) | 63.75 | 9.33 | 1.73 |

(iii) Mass m/z = 810(M+)

REFERENCE EXAMPLE 5

(i) 4'-O-benzylsulfonyl-3-deoxy-23-O-thexyldimethylsilyl-mycaminosyl tylonolide 9,20-bis(ethyleneacetal)

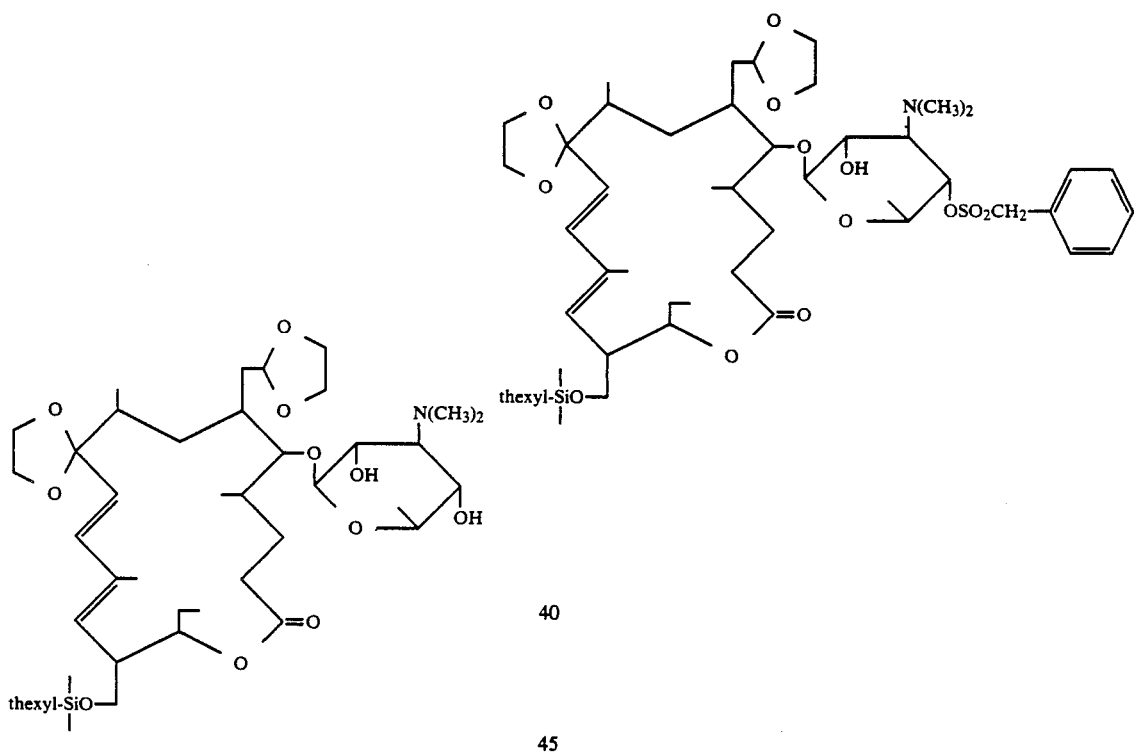

51 mg of 2',4'-O-acetyl-23-O-thexyldimethylsilyl-mycaminosyl tylonolide 9,20-bis(ethyleneacetal) was dissolved in 1.5 ml of methanol, and after adding thereto 0.5 ml of conc. aqueous ammonia, the mixture was kept at room temperature for 3 hours. The reaction solution was concentrated, and the residue was extracted with chloroform. The chloroform layer was concentrated; and the solid material thus obtained was dissolved in 1 ml of methanol, and kept at 50° C. overnight. The reaction solution was neutralized by using saturated aqueous sodium hydrogen carbonate, and extracted with chloroform. The organic layer was washed with saturated aqueous NaCl, dried, and concentrated to give pale yellow syrup material, which was purified by silica gel column chromatography (Wako gel C-200: 5 g; chloroform:methanol:conc.aqueous ammonia = 15:1:0.1) to give 39.9 (yield: 96%) of colorless solid material of 2-dehydro-2-en-3-deoxy-23-O-thexyldimethylsilyl-mycaminosyl tylonolide 9,20-bis(ethyleneacetal).

Physico-chemical character:
(i) $[\alpha]_D^{25}$: −34° (c1, CHCl$_3$)

1.30 g of 3-deoxy-23-O-thexyldimethylsilyl mycaminosyltylonolide 9,20-bis(ethyleneacetal) was dissolved in 26 ml of dry pyridine, and was cooled to −40° C. After adding thereto 459 mg of benzylsulfonyl chloride, the mixture was allowed to react for 3 hours. After adding thereto 0.5 ml of water, the temperature of the reaction mixture was allowed to become room temperature. After stirring the mixture for 1 hour, the mixture was concentrated. After adding thereto 100 ml of saturated aqueous sodium hydrogen carbonate, the mixture was extracted with chloroform. The organic layer was washed with saturated aqueous sodium chloride, dried over magnesium sulfate, and concentrated to give unstable pale yellow solid material (1.56 g).

(2)
3,4'-dideoxy-4'-iodo-23-O-thexyldimethylsilyl-mycaminosyl tylonolide, 9,20-bis(ethyleneacetal)

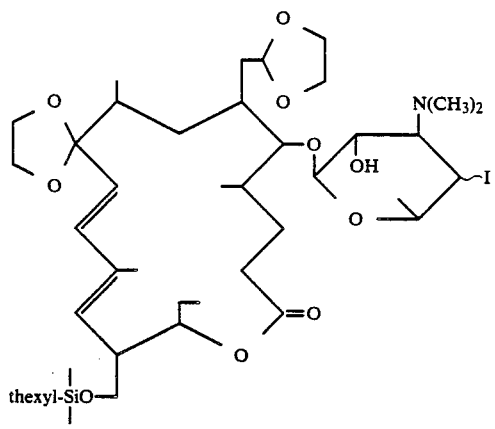

4'-O-benzylsulfonyl-3-deoxy-23-O-thexyldimethylsilyl-mycaminosyl tylonolide 9,20-bis(ethyleneacetal) [crude product, 1.56 g obtained at (1) above] was dissolved in 24 ml of dry 2-butanone, and after adding thereto 366 mg of sodium iodide, the mixture was stirred under heating under nitrogen gas atmosphere at 80° C. After 30 minutes, the reaction solution was filtered, and washed. The filtered solution and washing solution were combined, and concentrated. The residue was extracted with ethyl acetate. The organic layer was washed with saturated aqueous sodium hydrogen carbonate, 0.1M aqueous sodium thiosulfate and saturated aqueous sodium chloride, successively, dried over magnesium sulfate, and concentrated to give yellow syrup material. This material was purified by using silica gel column chromatography (Wako gel C-200; 80 g; cyclohexane:acetone=7:2) to give 3,4'-dideoxy-4'-ioso-23-O-thexyldimethylsilyl mycaminosyl tylonolide 9,20-bis(ethyleneacetal) as colorless solid material (1.04 g) [yield from (1) above: 71%].

Physico-chemical character:
(i) $[\alpha]_D^{20.5}$: $-73°$ (c1, CHCl$_3$)

| (ii) Elemental analysis (C$_{43}$H$_{76}$NO$_{10}$SiI) | | | |
|---|---|---|---|
| | C | H | N | I |
| Found (%) | 56.39 | 8.24 | 1.46 | 14.14 |
| Cacld. (%) | 56.01 | 8.31 | 1.52 | 13.76 |

(iii) Mass (FAB) m/z=922 (M+)

REFERENCE EXAMPLE 6

3,4'-dideoxymycaminosyl tylonolide dimethylacetal 300 mg of 3,4'-dideoxymycaminosyl tylonolide was dissolved in 5.0 ml of dry methanol, and after adding thereto 150 mg of p-toluenesulfonic acid, the mixture was allowed to react at room temperature for 1 hour. After adding thereto 0.12 ml of triethylamine, the reaction solution was concentrated. To the residue was added 15 ml of saturated aqueous sodium hydrogen carbonate, and the mixture was extracted with chloroform. The extract solution was washed, dried over magnesium sulfate, and concentrated to give foamy solid material. This material was purified by using silica gel column chromatography (Wako gel:C-200: 6 g; chloroform:methanol:conc. aqueous ammonia=10:1:0.1) to give 306 mg of 3,4'-dideoxymycaminosyltylonolide dimethylacetal (yield: 94%).

Physico-chemical character:
(i) $[\alpha]_D^{24}$: $+8°$ (c2, CHCl$_3$)

| (ii) Physico-chemical character: | | | |
|---|---|---|---|
| | C | H | N |
| Found (%) | 63.95 | 9.26 | 2.20 |
| Cacld. (%) | 63.84 | 9.42 | 2.25 |

(iii) Mass m/z=611(M+)

EXAMPLE 1

(1)
3-Deoxy-23-O-thexyldimethylsilylmycaminosyltylonolide 9,20-bis(ethyleneacetal)

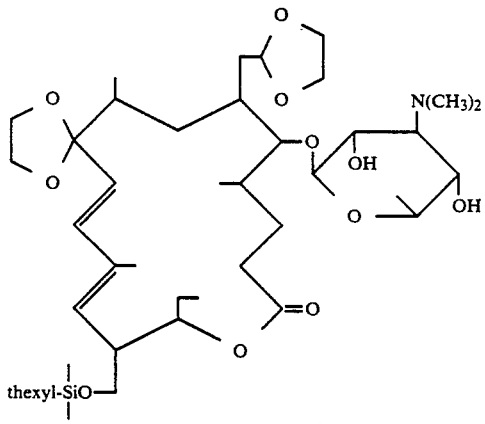

2.00 g (2.47 mmol) of 2-dehydro-2-en-3-deoxy-23-O-thexyldimethylsilylmycaminosyl tylonolide 9,20-bis(ethyleneacetal) was dissolved in dry toluene, and the mixture was cooled to $-60°$ C., and 7.4 ml of 1.5M diisobutylaluminum hydride toluene solution was poured into the above mixture under nitrogen gas stream under stirring. After 30 minutes, 3 g of sodium sulfate 10 H$_2$O was added to the mixture, the reaction was stopped, and after adding thereto 20 ml of water containing 1.33 ml of acetic acid, the temperature of the mixture was allowed to become room temperature. After adding thereto saturated aqueous sodium hydrogen carbonate and stirring, the mixture was extracted with chloroform. The organic layer thus obtained was washed with water, dried and concentrated to give colorless foamy solid material (1.95 g). This material was purified by using silica gel column chromatography (Wako gel C-200: 200 g; chloroform:methanol:conc. aqueous ammonia=18:1:0.1) to give 1.09 g of 3-deoxy-23-O-thexyldimethylsilil mycaminosyltylonolide 9,20-bis(ethyleneacetal) (yield: 55%) as colorless solid material.

Physico-chemical character:
(i) $[\alpha]_D^{21}$: $-52°$ (c1, CHCl$_3$)

| (ii) Elemental analysis (C$_{43}$H$_{77}$NO$_{11}$Si) | | |
|---|---|---|
| | C | H | N |
| Found (%) | 63.08 | 9.49 | 1.73 |

-continued

| (ii) Elemental analysis (C$_{43}$H$_{77}$NO$_{11}$Si) | | | |
|---|---|---|---|
| | C | H | N |
| Cacld. (%) | 63.59 | 9.56 | 1.72 |

(2) 3-Deoxy-mycaminosyltylonolide

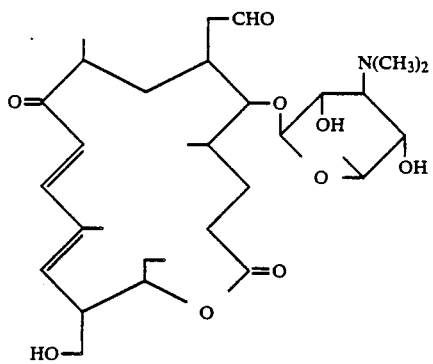

0.60 g of 3-deoxy-23-O-thexyldimethylsilyl mycaminosyltylonolide 9,20-bis(ethyleneacetal) was dissolved in 9 ml of tetrahydrofuran, and after adding thereto 1.13 ml of 1M tetrabutylammonium fluoride-tetrahydrofuran solution, the mixture was allowed to stand at room temperature. After confirming the termination of the de-silylation, the reaction solution was concentrated (1/5) and adding thereto 50 ml of saturated was extracted with choroform. The solution thus obtained was washed with water, dried and concentrated to give crude product of 3-deoxy-maycaminosyltylonolide-9,20-bis(ethyleneacetal). This product was dissolved in 6 ml of acetonitrile, and after adding thereto 24 ml of 0.1M aqueous hydrochloric acid, the formed white solution was stirred. After 6 hours, the uniform was obtained, and after adding thereto 60 ml of saturated aqueous sodium hydrogen carbonate, the mixture was extracted with chloroform. The organic layer thus obtained was concentrated to give pale yellow solid material. This material was purified by using silica gel column chromatography (Wako gel C-200: 40 g; Chloroform:methanol:conc. aqueous ammonia=15:1:0.1) to give 383 mg of colorless solid material of 3-deoxymycaminosyl tylonolide (yield: 89% from the product of Example 1 (1).

Physico-chemical character:
(i) $[\alpha]_D^{22}$: $-23°$ (c1, CHCl$_3$)

| (ii) Elemental analysis (C$_{31}$H$_{51}$NO$_9$.H$_2$O) | | | |
|---|---|---|---|
| | C | H | N |
| Found (%) | 62.29 | 8.80 | 2.29 |
| Cacld. (%) | 62.08 | 8.73 | 2.33 |

(iii) Mass m/z 582(M+)

(iv) $^1$H-nmr (CDCl$_3$, TMS) δ 0.94 (3H, t, 17 -CH$_3$), 0.98 (3H, d, 1 8 - CH$_3$), 1.22 (3H, d, 21 - CH$_3$), 1.25 (3H, d, 6'-CH$_3$), 1.85 (3H, d, 22-CH$_3$), 2.35 (1H, t, H-3'), 2.49 (6H, s, 3'-N (CH$_3$)$_2$), 3.02 (1H, t, H-4'), 3.23 (1H, dd, H-5'), 3.48 (1H, dd, H-2'), 4.23 (1H, d, H-1'), 4.88 (1H, m, H-15), 5.82 (1H, bd, H-13; H$_{13,14}$=10 Hz), 6.34 (1H, d, H-10; J$_{10,11}$=16 Hz), 7.30 (1H, d, H-11) 9.68 (1H, s, H-20)

EXAMPLE 2

(1)
3,4'-Dideoxy-23-O-thexyldimethylsilyl-mycaminosyl-tylonolide 9,20-bis(ethyleneacetal)

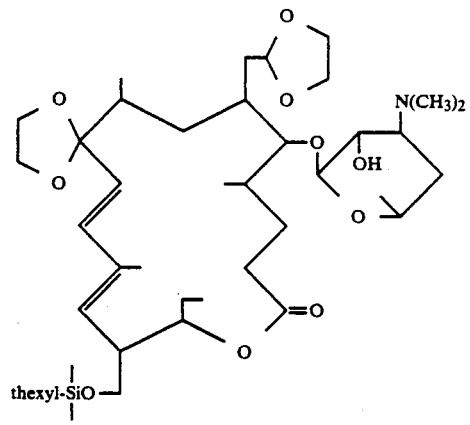

1.04 g of 3,4'-dideoxy-4'-iodo-23-O-thexyldimethylsilyl mycaminosyltylonolide 9,20-bis(ethyleneacetal) was dissolved in 20 ml of dry benzene, and adding thereto 0.91 ml (3.4 mmol) of tributyltin hydride and 37 mg of azodiisobutyyonitrile, the mixture was allowed to react for 2 hours at 80° C. After 2 hours, the reaction solution was concentrated, and the residue was purified by using silica gel column chromatography (Wako gel C-200: 50 g; cyclohexane:acetone=3:1→chloroform (600 ml)→chloroform:methanol:conc. aqueous ammonia=10:1:0.1) to give 0.79 g of colorless solid material of 3,4'-dideoxy-23-O-thexyldimethylsilyl-mycaminosyltylonolide 9,20-bis(ethyleneacetal). [yield: 88%]

Physico-chemical character:
(i) $[\alpha]_D^{20}$: $-38°$ (c1, CHCl$_3$)
(ii) Mass m/z=795(M+)

(2) 3,4'-Dideoxy-mycaminosyltylonolide

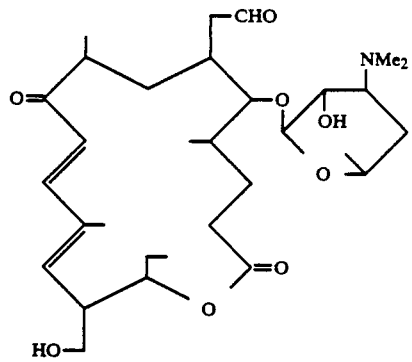

0.73 g of 3,4'-dideoxy-23-O-theyxldimethylsilyl mycaminosyltylonolide 9,20-bis(ethyleneacetal) was dissolved in 12 ml of tetrahydrofuran, and after adding thereto 1.65 ml of 1M tetrabutylammonium fluoride-tetrahydrofuran solution, the mixture was allowed to react for 5 hours. The reaction mixture was concentrated, and the residue was extracted with chloroform, and washed with saturated aqueous sodium hydrogen carbonate and saturated aqueous sodium chloride. The organic layer was dried over magnesium sulfate, and concentrated to give pale yellow solid material (0.72 g) of the crude product of 3,4'-dideoxy mycaminosyltylonolide 9,20-bis(ethyleneacetal). This product was dissolved in 8 ml of acetonitrile, and after adding thereto 24 ml of 0.1M aqueous hydrochloric acid, the mixture was allowed to react at 37° C. overnight. To the reaction solution was added 70 ml of saturated aqueous sodium hydrogen carbonate, and the mixture was extracted with chloroform. The extract solution was washed with saturated aqueous sodium hydrogen carbonate, dried over magnesium sulfate, and concentrated to give pale yellow syrup material. The material was purified by silica gel column chromatography (Wako gel C-200: 35 g; chloroform:MeOH:conc. aqueous ammonia=12:1:0.1) to give 3,4'-dideoxymycaminosyltylonolide (511 mg, colorless material) [yield: 99%].

Physico-chemical character:
(i) $[\alpha]_D^{19}$: −21° (c1, CHCl$_3$)

| (ii) Elemental analysis (C$_{31}$H$_{51}$NO$_8$.H$_2$O) | | | |
|---|---|---|---|
| | C | H | N |
| Found (%) | 63.81 | 8.80 | 2.50 |
| Cacld. (%) | 63.78 | 8.97 | 2.40 |

(iii) Mass m/z=566(M+)
(iv) $^1$H-nmr (CDCl$_3$, TMS) δ 0.94 (3H, t, 17-CH$_3$), 1.04 (3H, d, 18-CH$_3$), 1.85 (3H, d, 22-CH$_3$), 2.26 (6H, s, 3'-N(CH$_3$)$_2$), ~2.90 (1H, m, H-14), 3.19 (1H, dd, H-2'), 4.19 (1H, d, H-1'), 4.88 (1H, m, H-15), 5.83 (1H, d, H-13; J$_{13,14}$=10 Hz), 6.35 (1H, d, H-10; J$_{10,11}$=1.6 Hz), 7.30 (1H, d, H-11), 9.70 (1H, s, H-20)

EXAMPLE 3

(1)
9-Deoxo-3,4'-dideoxy-9-N-methoxyimino-mycaminosyltylonolide dimethylacetal

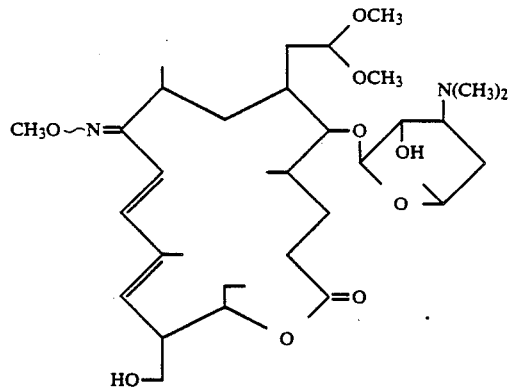

293 mg of 3,4'-dideoxy mycaminosyltylonolide dimeylacetal (0.48 mmol) was dissolved in dry methanol, and after adding thereto 85 μl (0.98 mmol) of dry pyridine and 81 mg (0.97 mmol) of methoxyamine hydrochloride, the mixture was allowed to react overnight. The reaction solution was concentrated, and after adding to the residue 15 ml of saturated aqueous sodium hydrogen carbonate, the mixture was extracted with chloroform, and the organic layer was washed with saturated aqueous sodium chloride, dried and concentrated to give foamy solid material (280 mg). This product is a mixture of two kinds of 9-N-methoxyimino compounds (5:1). This mixture was purified by silica gel column chromatography (Wako gel C-200: 50 g; choroform:methanol:conc. aqueous ammonia=15:1:0.1) to give colorless solid material of the main product of 9-deoxy-3,4'-dideoxy-9-N-methoxyimino-mycaminosyltylonolide dimethylacetal (163 mg).

Physico-chemical character:
(i) $[\alpha]_D^{22}$: −30° (c1, CHCl$_3$)

| (ii) Elemental analysis (C$_{34}$H$_{60}$N$_2$O$_9$.0.5H$_2$O) | | | |
|---|---|---|---|
| | C | H | N |
| Found (%) | 62.85 | 9.34 | 4.24 |
| Cacld. (%) | 62.83 | 9.46 | 4.31 |

(iii) Mass m/z=609 (M+)

(2)
9-Deoxo-3,4'-dideoxy-9-N-methoxyiminomycaminosyltylonolide

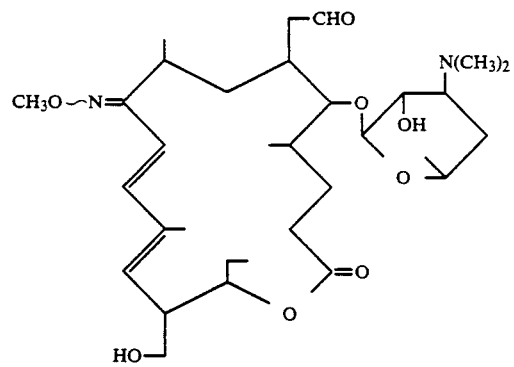

246 mg of 9-deoxy-3,4'-dideoxy-9-N--methoxyiminomycaminosyltylonolide dimethylacetal (two kinds of 9-N-methoxyimino compounds: mixture (5:1) was dissolved in 2.5 ml of acetonitrile, and after adding thereto 10 ml of 0.1M aqueous hydrochloric acid, the mixture was stirred for 4 hours at room temperature. The reaction solution was concentrated (⅓), and after adding thereto 25 ml of saturated aqueous sodium hydrogen carbonate, the mixture was extracted with chloroform. The extract solution was washed with saturated aqueous sodium chloride, dried and concentrated, and the solid material thus obtained was purified by silica gel column chromatography (Wake gel C-200: 30 g; chloroform:methanol:conc. aqueous ammoni=15:1:0.1) to give colorless solid material (205 mg) of 9-deoxo-3,4'-dideoxy-9-N-methoxyiminomycaminosyltylonolide (yield: 90%). This material is a mixture of two kinds of 9-N-methoxyimino compounds (5:1).

Physico-chemical character:
(i) $[\alpha]_D^{22}$: −50° (c1, CHCl$_3$)

In similar way to the above, 17 mg of the main product of 9-deoxy-3,4'-dideoxy-9-N-methoxyimino-mycaminosyltylonolide dimethylacetal was allowed to react and treated to give the main product of 9-deoxo-3,4'-dideoxy-9-N-methoxyimino-mycaminsyltylonolide.

Physico-chemical character:
(i) $[\alpha]_D^{22}$: −70° (c1, CHCl$_3$)
(ii) Mass m/z=595(M+)

EXAMPLE 4

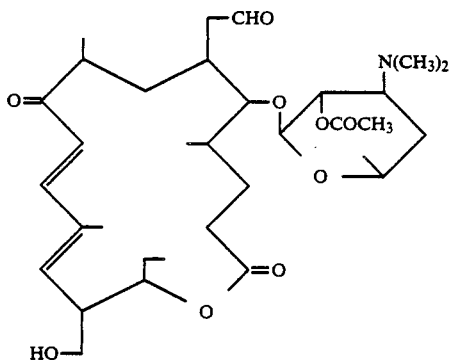

3.00 g of 3,4'-dideoxymycaminosyltylonolide was dissolved in 30 ml of dry acetonitrile, and after adding thereto 0.65 ml of acetic anhydride, the mixture was allowed to react at room temperature for 3 hours. The reaction solution was concentrated, and after adding 100 ml of saturated aqueous sodium hydrogen carbonate, the mixture was concentrated with ethyl acetate. The extract solution was washed with water, dried and concentrated to give pale yellow solid material. This material was purified by silica gel column chromatography (Wako gel C-200: 150 g; chloroform:methanol=10:1) to give 2.95 g (yield: 92%) of colorless solid material of 2'-O-acetyl-3,4'-dideoxymycaminosyl tylonolide.

Physico-chemical character:
$[\alpha]_D^{26}$: $-1°$ (c1, CHCl$_3$)

| (ii) Elemental analysis (C$_{33}$H$_{53}$NO$_9$.H$_2$O) | | | |
|---|---|---|---|
| | C | H | N |
| Found (%) | 63.40 | 8.47 | 2.12 |
| Cacld. (%) | 63.33 | 8.86 | 2.24 |

(iii) Mass m/z=608(M$^+$ +1)

(iv) $^1$H-nmr (CDCl$_3$, TMS internal standard) δ 2.06 (3H, s, 2'-OCOCH$_3$: CH$_3$) 2.26 (6H, s, 3' - N(CH$_3$)$_2$) ~3.7 (2H, m, H - 23 a, b) 4.24 (1H, d, H - 1') 4.75 (1H, dd, H - 2') 5.80 (1H, d, H - 13) 6.35 (1H, d, H - 10) 7.28 (1H, d, H - 11) 9.68 (1H, s, 20 - CHO)

EXAMPLE 5

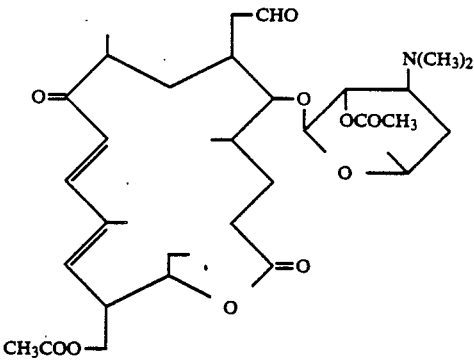

201 mg of 2'-O-acetyl-3,4'-dideoxy-mycaminosyl tylonolide was dissolved in 4 ml of dry pyridine, and after adding thereto 47 µl of acetic anhydride, the mixture was kept at room temperature for 10 hours. The reaction solution was concentrated, and poured into 20 ml of saturated aqueous sodium hydrogen carbonate. The mixture was extracted with toluene, and the organic layer was washed with water, dried and concentrated to give pale yellow syrup material. This material was purified by silica gel column chromatography (Wako gel C-200: 10 g; benzene:ethyl acetate=1:3) to give colorless solid material of 211 mg (yield: 98%) of 2',23-di-O-acetyl-3,4'-dideoxy-mycaminosyl tylonolide.

Physico-chemical property:
(i) $[\alpha]_D^{21}$: $-6°$ (c1, CHCl$_3$)

| (ii) Elemental analysis (C$_{35}$H$_{55}$NO$_{10}$) | | | |
|---|---|---|---|
| | C | H | N |
| Found (%) | 64.64 | 8.55 | 1.96 |
| Cacld. (%) | 64.69 | 8.53 | 2.16 |

(iii) Mass m/z=649(M$^+$)

(iv) $^1$H-nmr (CDCl$_3$, TMS internal standard) δ 2.06, 2.08 (each 3H, s, CH$_3$ of 2'-OCOCH$_3$, CH$_3$ of 23-O-COCH$_3$) 2.26 (6H, s, 3'-N(CH$_3$)$_2$) ~4.1 (2H, m, H - 23 a, b) 4.24 (1H, d, H - 1') 4.75 (1H, dd, H - 2') 5.78 (1H, d, H - 13) 6.35 (1H, d, H - 10) 7.27 (1H, d, H - 11) 9.68 (1H, s, 20 -CHO)

EXAMPLE 6

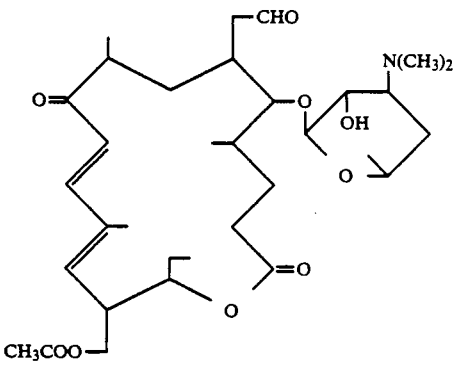

800 mg of 2',23-di-O-acetyl-3,4'-dideoxymycaminosyltylonolide was dissolved in 16 ml of methanol, and the mixture was allowed to stand for 5 hours at 50° C. The reaction solution was concentrated, and the residue was extracted with chloroform, washed with saturated aqueous sodium hydrogen carbonate and saturated aqueous sodium chloride successively, dried and concentrated to give pale yellow solid material. This material was purified by silica gel column chromatography (Wako gel C-200: 30 g; chloroform:methanol=10:1) to give 660 mg of colorless solid material of 23-O-acetyl-3,4'-dideoxy-mycaminosyltylonolide (yield: 88%).

Physico-chemical character:
(i) $[\alpha]_D^{21}$: $-18°$ (c1, CHCl$_3$)

| (ii) Elemental analysis (C$_{33}$H$_{53}$NO$_9$) | | | |
|---|---|---|---|
| | C | H | N |
| Found (%) | 65.26 | 8.93 | 2.10 |
| Cacld. (%) | 65.21 | 8.79 | 2.30 |

(ii) Mass m/z=608 (M$^+$ +1)

(iv) $^1$H-nmr (CDCl$_3$, TMS internal standard) δ 2.06 (3H, s, CH$_3$ of 23-OCOCH$_3$) 2.26 (6H, s, 3'-N(CH$_3$)$_2$) ~4.2 (3H, m, H - 1', H - 23 a, b) 5.79 (1H, d, H - 13) 6.36 (1H, d, H - 10) 7.30 (1H, d, H - 11) 9.70 (1H, s, 20 - CHO)

EXAMPLE 7

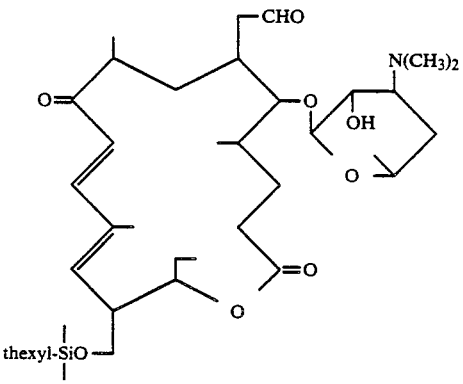

72 mg of 2'-O-acetyl-3,4'-dideoxy-mycaminosyltylonolide was dissolved in 1.4 ml of acetonitrile, and after adding thereto 14.5 mg of imidazole and 28 μl of thexyldimethylsilane chloride, the mixture was allowed to stand at room temperature overnight. (The reaction solution was concentrated somewhat.) After adding thereto 10 ml of saturated aqueous sodium hydrogen carbonate, the mixture was extracted with ethyl acetate. The organic layer was washed with water, dried and concentrated to give 93 mg of pale yellow syrup material. This material was dissolved in 2.0 ml of methanol, and the mixture was allowed to react at 50° C. for 5 hours. The reaction solution was concentrated, and the residue was extracted with chloroform. The extract solution was washed with saturated aqueous sodium hydrogen carbonate and saturated aqueous sodium chloride, successively, dried and concentrated to give pale yellow solid material. This material was purified by silica gel column chromatography (Wako gel C-200: 8 g; chloroform:methanol:conc. aqueous ammonia=17:1:0.1) to give 69 mg (yield: 85%) of 3,4'-dideoxy-23-O-thexyldimethylsilyl-mycaminosyltylonolide (colorless solid material).

Physico-chemical character:

(i) $[α]_D^{21}$: −20° (c1, CHCl$_3$)

(ii) Elemental analysis (C$_{39}$H$_{69}$NO$_8$Si·½H$_2$O)

| | C | H | N |
|---|---|---|---|
| Found (%) | 65.50 | 9.68 | 1.80 |
| Cacld. (%) | 65.32 | 9.70 | 1.96 |

(iii) Mass m/z=708 (M$^+$)

(iv) $^1$H-nmr (CDCl$_3$, TMS) δ 0.08 x 2 (3H, s, -Si(CH$_3$)$_2$ thexyl CH$_3$) 2.26 (6H, s, 3'-N(CH$_3$)$_2$) ~3.7 (2H, m, H - 23 a, b) 4.19 (1H, d, H - 1') 5.88 (1H, d, H - 13) 6.32 (1H, d, H - 10) 7.30 (1H, d, H - 11) 9.70 (1H, s, 20 - CHO).

What is claimed is:

1. A 3-deoxy-mycaminosyltylonolide compound of the following formula or its pharmaceutically acceptable salt:

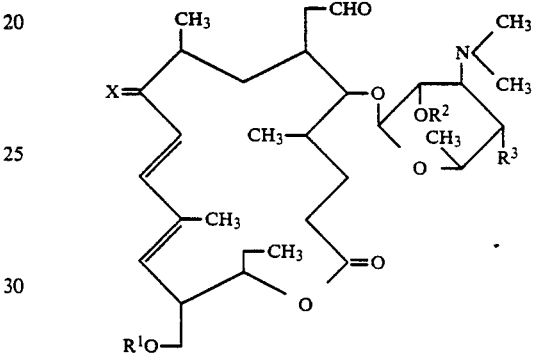

wherein X represents an oxygen atom; R$^1$ represents an alkylsilyl group; and R$^2$ and R$^3$ represent hydrogen.

2. A pharmaceutical composition having antibacterial activity comprised of an antibacterial effective amount of the compound of claim 1 and a pharmaceutically acceptable carrier.

3. The pharmaceutical composition of claim 2 wherein said compound is 3,4'-di-deoxy-23-O-thexyl-dimethylsilyl-mycaminosyltylonolide.

4. A method for inhibiting bacterial activity in a host which comprises administering to said host an antibacterial effective amount of the pharmaceutical composition of claim 2.

5. The method of claim 4 wherein said compound is 3,4'-di-deoxy-23-O-thexyldimethylsilyl-mycaminosyltylonolide.

* * * * *